US006200747B1

(12) United States Patent
Pergolizzi et al.

(10) Patent No.: US 6,200,747 B1
(45) Date of Patent: Mar. 13, 2001

(54) METHOD AND KITS FOR DETECTION OF FRAGILE X SPECIFIC, GC-RICH DNA SEQUENCES

(75) Inventors: Robert G. Pergolizzi, New Milford, NJ (US); Susan H. Erster, Setauket; W. Ted Brown, Port Washington, both of NY (US)

(73) Assignee: North Shore University Hospital Research Corp., Manhasset, NY (US)

( * ) Notice: Subject to any disclaimer, the term of this patent is extended or adjusted under 35 U.S.C. 154(b) by 0 days.

(21) Appl. No.: 07/827,691

(22) Filed: Jan. 28, 1992

(51) Int. Cl.[7] .......................................................... C12Q 1/68
(52) U.S. Cl. ................................................. 435/6; 536/23.5
(58) Field of Search ........................ 435/6, 91.2; 536/27, 536/235, 24.31, 24.33

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,804,748 | 2/1989 | Seela | 536/28 |
| 4,965,188 | 10/1990 | Mullis et al. | 435/6 |
| 5,066,584 | 11/1991 | Gyllensten et al. | 435/91 |
| 5,091,310 | 2/1992 | Innis | 435/91 |

OTHER PUBLICATIONS

Pieretti et al., Absence of Expression of the FMR–1 Gene in Fragile X Syndrome 66 Cell 817–822 (1991).
Richards et al., Fragile X Syndrome: Genetic Localization By Linkage Mapping of Two Microsatellite Repeats FRAXAC1 and FRAXAC2 Which Immediately Flank the Fragile Site, 28 J. Med. Genet. 818–823 (1991).
Richards et al., Fragile X Syndrome Diagnosis Using Highly Polymorphic Microsatellite Markers, 48 Am. J. Hum. Genet. 1051–1057 (1991).
Sutherland et al., Prenatal Diagnosis of Fragile X Syndrome By Direst Detection of the Unstable DNA Sequence, 325 N. Eng. J. Med. 1720–1722 (1991).
Heitz et al., Isolation of Sequences That Span the Fragile X and Identification of a Fragile X–Related CpG Island, 251 Science 1236–1239 (1991).
Hirst et al., Linear Order of New and Established DNA Markers around the Fragile Site at Xq27.3, 10 Genomics 243–249 (1991).
Djabali et al., Laser Microdissection of the Fragile X Region Identification of Cosmid Clones and of Conserved Sequences in this Region, 10 Genomics, 1053–1060 (1991).
Dobkin et al., Polymerase Chain Reaction Detection of the Dde I Polymorphism in the Factor 9 Gene for Fragile X Linkage Analysis, 38 Am. J. Med. Genet. 378–379 (1991).
Innis et al., DNA Sequencing with *Thermus aquaticus* DNA Polymerase and Direct Sequencing of Polymerase Chain Reaction–Amplified DNA, 85 Proc. Nat. Acad. Sci., U.S.A. 9346–9440 (1988).
Oberle, et al., Instability of a 550–Base Pair DNA Segment and Abnormal Methylation in Fragile X Syndrome, Science 252: 1097–1102, (1991).

(List continued on next page.)

*Primary Examiner*—Scott W. Houtteman
(74) *Attorney, Agent, or Firm*—Kenyon & Kenyon

(57) ABSTRACT

A method is provided for amplifying and detecting specific GC-rich nucleic acid sequences contained in a nucleic acid or in a mixture of nucleic acids, which includes treating a separate nucleic acid containing the specific sequence with a molar excess of primers and a polymerase and extending the primers in the presence of dATP, dCTP, TTP, and an analogue of dGTP. In one application of the present invention, individuals who are carriers for, or afflicted by, the fragile X syndrome are detected.

15 Claims, 3 Drawing Sheets

OTHER PUBLICATIONS

Kremer, et al., Mapping of DNA Instability at the Fragile X to a Trinucleotide Repeat Sequence p(CCG)n, Science 252: 1711–14, (1991).

Bell, et al., Physical Mapping across the Fragile X Hypermethylation and Clinical Expression of the Fragile X Syndrome, Cell 64: 861–66, (1991).

Verkerk, et al., Identification of a Gene (FMR–1) Containing a CGG Repeat Coincident with a Breakpoint Cluster Region Exhibiting Length Variation in Fragile X Syndrome, Cell 65: 905–14, (1991).

Rousseau et al., Direct Diagnosis by DNA Analysis of the Fragile X Syndrome of Mental Retardation, N.E. J. Med. 325: 1673–81 (1991).

Fu et al., Variations of the CGG Repeat at the Fragile X Site Results in Genetic Instability: Resolution of the Sherman Paradox, Cell 67: 1047–58 (1991).

Nakahori et al., Molecular Heterogeneity of the Fragile X Syndrome, Nucl. Acids Res. 19 4355–59, (1991).

Saiki, Primer–Directed Enzymatic Amplification of DNA with a Thermostable DNA Polymerase, Science 239: 487–91 (1988).

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
      (A) ORGANISM: Homo sapiens
      (F) TISSUE TYPE: Blood and amniotic cells
      (G) CELL TYPE: Lymphocyte (vii) IMMEDIATE SOURCE:
      (B) CLONE: FMR-1

(viii) POSITION IN GENOME:
      (A) CHROMOSOME/SEGMENT: X
      (B) MAP POSITION: 1-21

(x) PUBLICATION INFORMATION:
      (A) AUTHORS: Verkerk, A. JMH
      (B) TITLE: Identification of a Gene (FMR-1) Containing a

```
            CGG Repeat Coincident with a Breakpoint Cluster
            Region Exhibiting Length Variation in Fragile X
            Syndrome
      (C) JOURNAL: Cell
      (D) VOLUME: 65
      (F) PAGES: 905-914
      (G) DATE: 1991
      (K) RELEVANT RESIDUES IN SEQ ID NO:1: FROM 1 TO (xi) SEQUENCE DESCRIPTION: SEQ ID NO:1:

GACGGAGGCG CCCGTGCCAG G                                            21

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens
        (F) TISSUE TYPE: Blood and amniotic cells
        (G) CELL TYPE: Lymphocyte (vii) IMMEDIATE SOURCE:
        (B) CLONE: FMR-1

(viii) POSITION IN GENOME:
        (A) CHROMOSOME/SEGMENT: X
        (B) MAP POSITION: 181-203

(x) PUBLICATION INFORMATION:
        (A) AUTHORS: Verkerk, A. JMH
        (B) TITLE: Identification of a Gene (FMR-1) Containing a
            CGG Repeat Coincident with a Breakpoint Cluster
            Region Exhibiting Length Variation in Fragile X
            Syndrome
        (C) JOURNAL: Cell
        (D) VOLUME: 65
        (F) PAGES: 905-914
        (G) DATE: 1991
        (K) RELEVANT RESIDUES IN SEQ ID NO:2: FROM 1 TO (xi) SEQUENCE DESCRIPTION: SEQ ID NO:2:

TCCTCCATCT TCTCTTCAGC CCT                                          23

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (F) TISSUE TYPE: Blood and amniotic cells
        (G) CELL TYPE: Lymphocyte (vii) IMMEDIATE SOURCE:
        (B) CLONE: FMR-1
```

-continued

```
   (viii) POSITION IN GENOME:
           (A) CHROMOSOME/SEGMENT: X
           (B) MAP POSITION: 127-151

(x) PUBLICATION INFORMATION:
           (A) AUTHORS: Verkerk, A. JMH
           (B) TITLE: Identification of a Gene (FMR-1) Containing a
               CGG Repeat Coincident with a Breakpoint Cluster
               Region Exhibiting Length Variation in Fragile X
               Syndrome
           (C) JOURNAL: Cell
           (D) VOLUME: 65
           (F) PAGES: 905-914
           (G) DATE: 1991
           (K) RELEVANT RESIDUES IN SEQ ID NO:3: FROM 1 TO (xi) SEQUENCE DESCRIPTION: SEQ ID NO:3:

CTGGGCCTCG AGCGCCCGCA GCCCA                                            25

(2) INFORMATION FOR SEQ ID NO:4:

(i) SEQUENCE CHARACTERISTICS:
           (A) LENGTH: 90 base pairs
           (B) TYPE: nucleic acid
           (C) STRANDEDNESS: single
           (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
           (A) ORGANISM: Homo sapiens
           (F) TISSUE TYPE: Blood and amniotic cells
           (G) CELL TYPE: Lymphocyte (vii) IMMEDIATE SOURCE:
           (B) CLONE: FMR-1

(viii) POSITION IN GENOME:
           (A) CHROMOSOME/SEGMENT: X
           (B) MAP POSITION: 37-126

(x) PUBLICATION INFORMATION:
           (A) AUTHORS: Verkerk, A. JMH
           (B) TITLE: Identification of a Gene (FMR-1) Containing a
               CGG Repeat Coincident with a Breakpoint Cluster
               Region Exhibiting Length Variation in Fragile X
               Syndrome
           (C) JOURNAL: Cell
           (D) VOLUME: 65
           (F) PAGES: 905-914
           (G) DATE: 1991
           (K) RELEVANT RESIDUES IN SEQ ID NO:4: FROM 1 TO (xi) SEQUENCE DESCRIPTION: SEQ ID NO:4:

CGGCGGCGGC GGCGGCGGCG GCGGCGGCGG CGGCGGCGGC GGCGGCGGCG GCGGCGGCGG     60

CGGCGGCGGC GGCGGCGGCG GCGGCGGCGG                                      90
```

METHOD AND KITS FOR DETECTION OF FRAGILE X SPECIFIC, GC-RICH DNA SEQUENCES

FIELD OF THE INVENTION

This invention relates generally to methods for amplifying, detecting and cloning nucleic acid sequences, particularly to methods that are based on a polymerase chain reaction (PCR). It relates to a process for amplifying nucleic acid sequences in a test sample. One can also employ the present invention to determine whether a specific nucleic acid sequence is present in a test sample. More specifically, this invention relates to a process for amplifying a selected GC-rich nucleic acid sequence to facilitate detection and/or cloning of the sequence. The process of the present invention uses, in one embodiment, a thermostable polymerase to catalyze the extension of a primer bound to a template. The present invention also relates to the development of diagnostic assays for inherited or sporadic genetic defects. One application of the present invention provides an assay for the genetic defect that causes the fragile X syndrome in carriers, persons afflicted, fetuses and embryos.

BACKGROUND

The fragile X syndrome is the most common inherited form of mental retardation and developmental disability. This condition afflicts approximately 1 in 1250 males and 1 in 2000 females.

As the name implies, fragile X is an X chromosome-linked condition. The fragile X phenotype is characterized by a visible constriction near the end of the X chromosome, at locus q27.3, and there is a tendency for the tip of the X-chromosome to break off under certain conditions in tissue culture. These tissue culture procedures form the basis of the assay most commonly used for fragile X at present.

The pattern of inheritance of this condition is atypical of that associated with X-linked conditions. Typically, there is a 50% probability that the son of a woman who carries an X-linked genetic defect will be afflicted by the defect. Additionally, all males who carry the abnormal gene are afflicted by the X-linked condition in the typical pattern. Furthermore, since females have two X chromosomes, they normally do not suffer the effects of a single damaged X chromosome.

In fragile X, however, some carrier males are phenotypically normal. Moreover, about one third of the females who inherit the fragile X chromosome are afflicted. The incidence of carrier males in different generations of a family varies. Daughters of carrier males are generally non-expressing carriers, but may have afflicted sons. Furthermore, afflicted daughters occur more frequently among the offspring of carrier mothers than among the offspring of carrier fathers (Brown, *The Fragile X: Progress toward Solving the Puzzle*, Am. J. Human Genet. 47 175–80, 1990).

Researchers recently identified the genomic region associated with this condition. (Oberle, et al., *Instability of a 550-Base Pair DNA Segment and Abnormal Methylation in Fragile X Syndrome*, Science 252 1097–1102, 1991; Kremer, et al., *Mapping of DNA Instability at the Fragile X to a Trinucleotide Repeat Sequence p(CCG)n*, Science 252 1711–14, 1991; and Bell, et al., *Physical Mapping across the Fragile X Hypermethylation and Clinical Expression of the Fragile X Syndrome*, Cell 64 861-66, 1991). Additionally, researchers have sequenced a partial cDNA clone derived from this region, called FMR-I. (Verkerk, et al., *Identification of a Gene (FMR-1) Containing a CGG Repeat Coincident with a Breakpoint Cluster Region Exhibiting Length Variation in Fragile X Syndrome*, Cell 65 905–14, 1991). The Oberle, Kremer, Bell and Verkerk papers are hereby incorporated by reference.

These studies provide an explanation for the atypical pattern of inheritance of fragile X. The mutation that ultimately results in the fragile X phenotype occurs in stages. In the early stages, the gene is not fully defective, rather there is a "pre-mutation" of the gene. Carriers of the premutation have a normal phenotype. A further mutation occurs in carrier females that produces the phenotype in their offspring.

The coding sequence for FMR-I contains a variable number of CGG repeats. Individuals who are not carriers have approximately 30 CGG repeats in their FMR-I. Carriers, however, have between 50 and 200 CGG repeats. This amplification of the FMR-I CGG sequence is the pre-mutation. Afflicted individuals have even more CGG repeats. As many as several thousand CGG repeats have been observed in afflicted individuals. (Oberle, et al., 1991).

However, most affected individuals do not express the FMR-1 mRNA (Pieretti, et al., Absence of Expression of the FMR-1 Gene in Fragile X Syndrome, Cell 66 1–201991). A CpG island, located upstream of the CGG repeat region, is methylated when the number of CGG repeats is above a threshold of about 200 copies (Oberle, et al., 1991; Kremer, et al., 1991, Bell, et al., 1991). This methylation inactivates the gene.

Until now, the only way to diagnose the fragile X syndrome has been to examine microscopically an afflicted individual's chromosomes after cell growth and treatment in tissue culture. In such an examination, the laboratory examined the X chromosome to ascertain whether it was characteristically constricted, or had a broken tip. This method is both costly and not reliable. For example, this method misses almost all male carriers and half of the female carriers of the fragile X syndrome. (THE FRAGILE X SYNDROME, Oxford Univ. Press (Davies, ed. 1989)) Another method for detecting fragile X carriers and genotypes employs a Southern blot methodology but lacks sensitivity and speed. (Rousseau et al. Direct Diagnosis by DNA Analysis of the Fragile X Syndrome of Mental Retardation, N.E. J. Med. 1673–81 (1991))

The present invention provides a fast, inexpensive genetic test for reliably identifying carriers of the fragile X genotype based on molecular structure of the gene defect. The method of the present invention determines whether the number of CGG repeats in the test individual's X-chromosome are characteristic of a normal, carrier or afflicted person.

The test method of the present invention is based on the polymerase chain reaction (PCR). PCR-based assays are ideal for detecting specific DNA sequences that are present in low abundance relative to the total DNA. In brief, a PCR method amplifies the specific DNA sequence, for example, one hundred thousand to a million fold. Once amplified to this level, the specific DNA sequence, if present, is readily detected.

Prior attempts to develop PCR-based methods to directly identify the CGG repeat sequence at the genomic level have been unsuccessful (Kremer, et al., 1991), or only partially successful (Fu et al. Variations of the CGG Repeat at the Fragile X Site Results in Genetic Instability: Resolution of the Sherman Paradox, Cell 67: 1047–58 (1991)). This region appears unstable and difficult to clone or to analyze directly.

The inability of PCR-based methods to detect GC-rich sequences has hindered the development of an assay for other conditions. For example, clonality in Epstein-Barr virus infection, the androgen receptor gene, the beta-adrenergic receptor and the CMV genome are each characterized by a GC-rich nucleic acid sequence. It has not been possible to identify clonality of the Epstein-Barr virus with conventional PCR methods. Moreover, as the androgen receptor has a CAG repeat region, the beta-adrenergic receptor has an 80% GC rich region and the CMV genome has portions that are more than 75% GC, none of these nucleic acids are amplifiable by conventional PCR methods.

We have solved the problem of using PCR-based methods with GC-rich nucleic acid sequences. Using our method, we have amplified and detected the GC-rich region of the FMR-1 gene in normals, carriers and afflicted individuals.

SUMMARY OF THE INVENTION

The present invention amplifies selected GC-rich nucleic acid sequences present in a test sample. In one embodiment of the present invention, 7-deaza dGTP was substituted for dGTP.

The present invention can be used to assay for the GC-rich nucleic acid sequence characteristic of carriers of, and persons afflicted with, the fragile X syndrome.

DETAILED DESCRIPTION OF THE INVENTION

Figure 1:
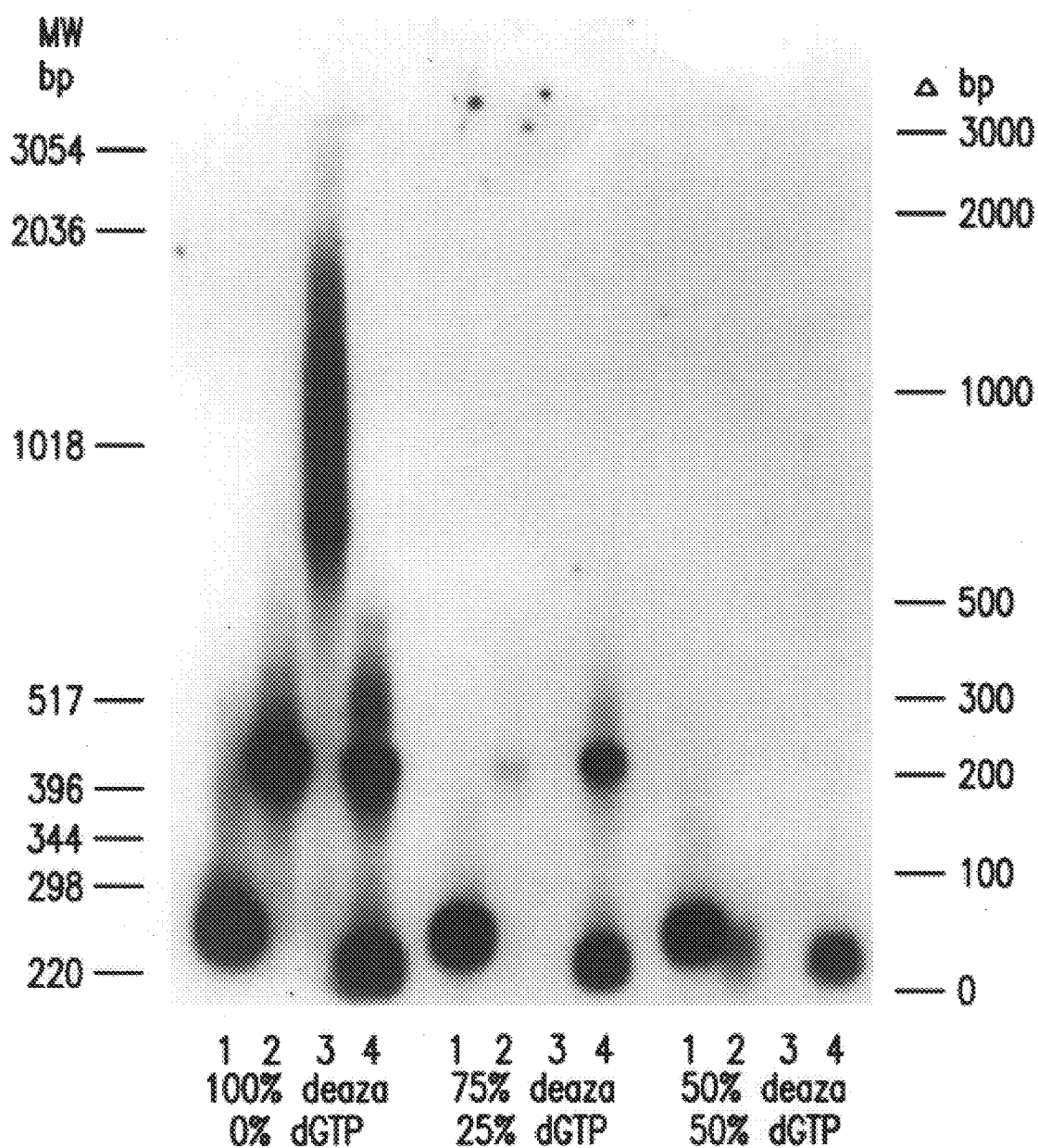
FIG. 1 is a photograph of an autoradiogram of PCR products which were synthesized in the presence of three different ratios of 7-deaza dGTP to dGTP resolved by electrophoresis and Southern blot hybridization.

U.S. Pat. Nos. 4,683,202; 4,683,195; 4,800,159 and 4,965,188, which are hereby incorporated by reference, provide additional details of the PCR process which is modified by the present invention.

Oligonucleotide such as those comprised of two or more deoxyribonucleotides or ribonucleotides, preferably more than three are useful in the practice of the present invention. An oligonucleotide's size and sequence determines its function or use. An oligonucleotide may be derived synthetically or by cloning.

Primer useful in the present invention include oligonucleotides capable of acting as a point of initiation of DNA or RNA synthesis. A primer may be purified from a restriction digest by conventional methods, or it may be produced synthetically.

PCR typically employs two primers that bind to a selected nucleic acid template. The primers are combined with the other PCR reagents under conditions that induce primer extension, i.e., with four different nucleoside triphosphates (or analogues thereof), an appropriate polymerase and an appropriate buffer ("buffer" includes pH, ionic strength, cofactors, etc.) at a suitable temperature. In a PCR method where the polymerase is Taq polymerase, the buffer preferably contains 1.5–2 mM of a magnesium salt, preferably $MgCl_2$, 150–200 $\mu M$ of each nucleoside, triphosphate (or analog thereof), 1 $\mu M$ of each primer, preferably with 50 mM KCl, 10 mM Tris buffer at pH 8.4, and 100 $\mu g/ml$ gelatin.

The primer is preferably single stranded for maximum efficiency in amplification, but it may be double stranded. Double stranded primers are first "denatured", i.e. treated to separate its strands before being used to prepare extension products. A preferred means of denaturing double stranded nucleic acids is by heating.

In the present invention, a primer must be sufficiently long to "prime" the synthesis of extension products in the presence of an appropriate polymerase and other reagents. The primer length depends on many factors, including the temperature and source of the primer and the use of the method. Typically, in the practice of the present invention, the primer contains 15–25 or more nucleotide residues. Short primer molecules generally require lower reaction temperatures to form and maintain the primer-template complexes which support the chain extension reaction.

The primers used in the present method are "substantially" complementary to a nucleic acid containing the selected sequence to be amplified, i.e. the primers must bind to, or hybridize with, a nucleic acid containing the selected sequence (or its complement). Nonetheless, the primer sequence need not be an exact complement of the template. For example, a non-complementary nucleotide fragment may be attached to the 5' end of the primer, with the remainder of the primer sequence being complementary to the nucleic acid containing the selected sequence. Alternatively, one or more non-complementary bases can be interspersed into the primer, provided that the primer sequence has sufficient complementarity with the sequence of the nucleic acid containing the selected sequence to (i) hybridize therewith and (ii) support a chain extension reaction. Notwithstanding the above, primers which are fully complementary to the nucleic acid containing the selected sequence are preferred to obtain the best results.

Any specific nucleic acid sequence can be produced by the present process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater can be the specificity of the primers for the target nucleic acid sequence, and thus the greater the efficiency of the process.

In a preferred embodiment of the present invention, two primers are used. One of the primers is complementary to (i) a sequence at the 3' end of the selected sequence, (ii) a sequence which abuts, or is near the 3' end of the selected sequence, or (iii) a sequence which includes the 3' end of the selected sequence as well as a sequence which abuts the 3' end of the selected sequence. The other primer, in this preferred embodiment, contains (i) the sequence at the 5' end of the selected sequence (ii) a sequence which abuts or is near the 5' end of the selected sequence or (iii) the sequence at the 5' end of the selected sequence as well as the sequence which abuts the 5' end of the selected sequence. Alternatively, either primer may be replaced by a primer which binds to, or hybridizes with, the complement of any of the foregoing preferred primers.

The terms "restriction endonucleases" and "restriction enzymes" refer to enzymes, commonly from bacteria, that cut double-stranded DNA at or near a specific nucleotide sequence.

The term "thermostable enzyme" refers to a polymerase which is heat stable and resistant and which catalyzes the formation of primer extension products complementary to a template. Generally, the synthesis will be initiated at the 3' end of each primer and will proceed in the 5' to 3' direction along the template strand, until synthesis terminates. Theoretically, this process produces DNA or RNA copies of different lengths. There may be thermostable enzymes which are useful in the present invention, which initiate synthesis at the 5' end and proceed in the other direction, using the process described above.

The thermostable enzyme herein must satisfy a single criterion to be effective for the amplification reaction of this invention, i.e., the enzyme must not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° C. to about 105° C. for a time depending mainly on the temperature and the nucleic acid length, typically about one half to four minutes. Higher temperatures may be tolerated as the buffer salt concentration and/or GC composition of the nucleic acid is increased. Preferably, the enzyme will not become irreversibly denatured at about 90–100° C.

The thermostable enzyme herein preferably has an optimum temperature at which it functions which is higher than about 40° C., which is the temperature below which hybridization of primer to template is promoted, although, depending on (1) the concentration of magnesium and other salts in the buffer and (2) the composition and the length of the primer, hybridization can occur at higher temperatures (e.g., 45–70° C.). The higher the enzyme's optimum temperature, the more specific and/or selective the primer-directed extension process is. However, enzymes that are active below 40° C., e.g., at 37° C., are also within the scope of this invention. Preferably, the optimum temperature ranges from about 50 to 80° C., more preferably above about 60° C.

Examples of enzymes which have been reported in the literature as being resistant to heat include heat-stable polymerases, such as, e.g., polymerases extracted from the thermostable bacteria *Thermus flavus, Thermus ruber, Thermus thermophilus, Bacillus stearothermophilus* (which has a somewhat lower temperature optimum than the others listed), *Thermus aquaticus, Thermus lacteus, Thermus rubens*, and *Methanothermus fervidus*.

Other useful polymerases are those which can withstand repeated cycles in which DNA is denatured and then annealed with a primer by means other than heat denaturation. Nonetheless, unstable polymerases can be employed where additional enzyme is added with each cycle.

The present invention is directed to a process for amplifying selected nucleic acid sequences. Because large amounts of the selected sequence may be produced by this process, the present invention may be used for improving the efficiency of cloning DNA or messenger RNA and for amplifying a selected sequence to facilitate detection thereof.

In general, the present process involves a chain reaction for producing, in exponential quantities relative to the number of reaction steps involved, at least one selected nucleic acid sequence given (a) that the ends of the selected sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the primers employed.

Any nucleic acid, in purified or non-purified form, can be utilized as the starting material. However, if the sample lacks the selected sequence, the process should not amplify any sequence. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The selected nucleic acid sequence to be amplified may be only a fraction of a larger molecule, or it may be present initially as a discrete molecule where the selected sequence constitutes the entire nucleic acid.

The selected sequence need not be purified; it may be a minor fraction of a complex mixture, such as a portion of the FMR-1 gene contained in human genomic DNA. The starting nucleic acid may contain two or more selected nucleic acid sequences, which may be the same or different. Therefore, the present process is useful not only for producing large amounts of one specific nucleic acid sequence, but also for amplifying simultaneously two or more selected nucleic acid sequences located on the same or different nucleic acid molecules.

The nucleic acid or acids may be obtained from any source, for example, from plasmids, from cloned DNA or RNA, or from natural DNA or RNA from any source, including bacteria, yeast, viruses, organelles, and higher organisms such as plants or animals. DNA or RNA may be extracted from any nucleic acid containing sample such as blood, tissue material such as chorionic villi or amniotic cells by a variety of techniques such as that described by Maniatis et al., Molecular Cloning: A Laboratory Manual (1982), 280–281.

For the process using sequence-specific probes to detect the amplified material, the cells may be directly used without purification of the nucleic acid. For example, a cellular sample can be suspended in hypotonic buffer and heated to about 90–100° C., until cell lysis and dispersion of intracellular components occurs. Such a process generally takes from about 1 to 15 minutes. After the heating step, the amplification reagents may be added directly to the lysed cells.

If the nucleic acid contains two strands, it is necessary to separate the strands of the nucleic acid before it can be used as the template. This strand separation can be accomplished by any suitable denaturing method including physical, chemical or enzymatic means. One preferred physical method of separating the strands of the nucleic acid involves heating the nucleic acid until it is completely (>99%) denatured. Typical heat denaturation involves temperatures ranging from about 90 to 105° C. for times generally ranging from about 0.5 to 5 minutes. Preferably the effective denaturing temperature is about 90–100° C. for about 0.5 to 3 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, CSH-Quantitative Biology, 43:63 (1978), and techniques for using RecA are reviewed in C. Radding, Ann. Rev. Genetics., 16:405–37 (1982). The denaturation produces two separated complementary strands of equal or unequal length.

If the double-stranded nucleic acid is denatured by heat, the reaction mixture is allowed to cool to a temperature which promotes hybridization of each primer present to its complementary target (template) sequence. This temperature is usually from about 35° C. to about 65° C. or higher, depending on reagents, preferably from about 37° C. to about 60° C., maintained for a time effective to denature the double-stranded nucleic acid, generally from about 0.5 to 5 minutes, and preferably about 1–3 minutes. In practical terms, the temperature is simply lowered from about 95° C. to about 65° C. or to as low as about 37° C., preferably to about 45–58° C. for Taq polymerase, and hybridization occurs at a temperature within this range.

Whether the nucleic acid is single- or double-stranded, the thermostable enzyme may be added at the denaturation step or when the temperature is being reduced to or is in the range for promoting hybridization. The reaction mixture is then heated to a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80° C. to 90° C.).

Depending mainly on the types of enzyme and nucleic acid(s) employed, the typical temperature effective for this synthesis reaction generally ranges from about 40 to 80° C., and preferably about 50 to 75° C. The temperature more preferably ranges from about 65 to 75° C. when a polymerase from Thermus aquaticus is employed. The period of time required for this synthesis may range from about 0.5 to 40 minutes or more, depending mainly on the temperature, the length of the nucleic acids, the enzyme and the complexity of the nucleic acid mixture, preferably about one to three minutes. If the nucleic acid is longer, a longer period of time is generally required.

The newly synthesized strand and its complementary nucleic acid strand form a double-stranded molecule which is used in the succeeding steps of the process. In the next step, the strands of the double-stranded molecule are separated by heat denaturation at a temperature effective to denature the molecule, but not so high that the thermostable enzyme is completely and irreversibly denatured or inactivated. Depending mainly on the type of enzyme and the length of nucleic acid, this temperature generally ranges from about 90 to 105° C., more preferably about 90 to 100° C., and the time for denaturation typically ranges from about one half to four minutes, depending mainly on the temperature and the nucleic acid length.

After this time, the temperature is decreased to a level which promotes hybridization (or annealing) of the primer to its complementary single-stranded molecule (template) produced from the previous step. Such temperature is described above.

After this hybridization step, or in lieu of (or concurrently with) this hybridization step, the temperature is adjusted to a temperature which is effective to promote the activity of the thermostable enzyme to enable synthesis of a primer extension product using as a template the newly synthesized strand from the previous step. The temperature again must not be so high as to separate (denature) the extension product from its template, as previously described (usually from about 40 to 80° C. for about 0.5 to 40 minutes, preferably about 50 to 70° C. for about 1 to 3 minutes). Hybridization may occur during this step, so that the previous step of cooling before denaturation is not required. In such a case, using simultaneous steps, the preferred temperature range is between about 50 to 70° C.

The heating and cooling steps of strand separation, hybridization, and extension product synthesis can be repeated as often as needed to produce the desired quantity of the specific nucleic acid sequence, depending on the ultimate use. The only limitation is the amount of the primers, the thermostable enzyme and the nucleoside triphosphates present. Preferably, the steps are repeated at least once. For use in detection, the number of cycles will depend, e.g., on the nature of the sample. If the sample is a complex mixture of nucleic acids and the total nucleic acid is held constant, more cycles will be required to amplify the signal sufficiently for its detection. For general amplification and detection, preferably the process is repeated at least about 20 times.

The process of the present invention uses an analogue of guanosine nucleotide. U.S. Pat. No. 4,804,748 discloses analogues useful in the present invention and is hereby incorporated by reference. Preferred analogues include inosine, 7-deaza-guanosine and 7-deaza inosine nucleotides (both ribo- and deoxyribo-). The 2'-deoxy analogues are more preferred and the 7-deaza-2'-deoxy guanosine (7-deaza-2'-dGTP) analogue is further preferred.

In addition to using an analogue of guanosine, it is further preferred that the method of the present invention is performed in a reaction mixture that is substantially free of both GTP and dGTP.

In the preferred embodiment, the polymerizations, or chain extension reaction, is performed in standard PCR buffer (50 mM Kcl, 10 mM Tris-Hcl, pH 8.3, 15 mM $MgCl_2$, 0.001% (w/v) gelatin, (Saiki, Primer-Directed Enzymatic Amplification of DNA with a Thermostable DNA Polymerase, Science 239: 487–91 (1988)) with the addition of 0.5–1 µg denatured genomic DNA, 50 pmoles of each oligonucleotide primer, 2.5 units of Taq polymerase, and 10% DMSO. The reaction contained 320 µM each of dATP, dCTP and dTTP, but was modified such that 320 µm 7-deaza-2'-dGTP was used in place of dGTP.

The following examples refer to the use of the invention to detect the presence of amplified GC-rich sequences in individuals afflicted with the fragile X syndrome, in male and female carriers of the pre-mutation for this condition, and in control individuals.

The GTP analog used in these examples was 7-deaza-2'-dGTP. However, when 7-deaza-2'-GTP was diluted with dGTP under the conditions employed in these examples, the higher molecular weight species were not detected (FIG. 1). Thus, it is preferred that the PCR reaction mixture is substantially free of GTP and dGTP.

In alternative embodiments of the present invention, other constituents which improve the replication or transcription of GC rich nucleic acids such as DMSO and glycerol are employed.

Conventional cloning and expression procedures can be adapted to employ the PCR method of the present invention. For example, in a conventional process for cloning one or more selected nucleic acids that are GC rich, a DNA can be amplified in quantity before cloning by using a PCR process that is substantially free of GTP and dGTP, but contains an analog of GTP or dGTP. Such a process might include: (i) adding a restriction enzyme to the product of the amplified nucleic acid in a manner effective to obtain cleaved products containing a selected DNA sequence; (ii) ligating such a cleaved product containing said selected DNA sequence in a manner effective to make a recombinant molecule; (iii) purifying, desalting and/or concentrating such cleaved products; (iv) sequencing said recombinant molecule containing the selected DNA sequence; (v) expressing the protein encoded by the specific nucleic acid sequence; and (vi) ligating such cleaved products into a new nucleic acid in a specific orientation.

Several individuals afflicted with the fragile X syndrome and some of the members of their families were analyzed using our modified PCR assay. In some cases, genomic DNA was isolated from peripheral blood lymphocytes or cultured amniotic cells obtained from the afflicted individuals and their family members. Other samples were obtained directly from amniotic fluid without culture, or from crude cell lysates without DNA extraction. Methods for isolating genomic DNA are described in more detail in Kunkel, *Analysis of Human Y Chromosome Specific Reiterated DNA in Chromosome Variants*, Pro. Nat'l Acad. Sci. 74: 1245–49 (1977), which is hereby incorporated by reference.

Oligodeoxyribonucleotide primers specific for a portion of the published FMR-I cDNA sequence (Verkerk, et al., 1991) were synthesized by cyanoethyl phosphoramidite Chemistry on a Biosearch/Milligen Model 8700 DNA Synthesizer and purified by HPLC. The sequence of the sense primer was 5' GACGGAGGCGCCCGTGCCAGG 3' (corresponding to nucleotides 1–21 of the FMR-I cDNA sequence) and that of the antisense primer was 5' TCCTC-CATCTTCTCTTCAGCCCT 3' (corresponding to nucleotides 203–181 of the FMR-I cDNA sequence). Based on the published sequence (Verkerk, et al. 1991) and our primer selection, the amplified product was predicted to be 203 bp long and to contain a 90 bp CGG-rich region. The Verkerk reference is hereby incorporated by reference.

The PCR amplifications were performed in standard PCR buffer (50 mM Kcl, 10 mM Tris-Hcl, pH 8.3, 15 mM $MgCl_2$, 0.001% (w/v) gelatin) with the addition of 0.5–1 ug denatured genomic DNA, 50 pmoles of each oligonucleotide primer, 2.5 units of Taq polymerase, and 10% DMSO. The reaction contained 320 $\mu$M each of dATP, dCTP and TTP, but was modified such that 320 $\mu$M 7-deaza-2'-dGTP was used in place of dGTP. Use of this modified nucleotide significantly increased the amount of specific PCR product generated with this set of primers and permitted amplification and detection of the very large alleles present in affected individuals, the detection of which alleles is not possible by the prior methods. The reactions were subjected to 40 cycles of denaturation at 97° C. for 30 sec, annealing at 55° C. for 60 sec and elongation at 72° C. for 60 sec.

An aliquot of each reaction was analyzed by agarose gel electrophoresis. The PCR products could not be directly visualized by ethidium bromide staining, so Southern blot analysis was used to increase the visibility of these products. The DNA was transferred to a nylon membrane. The membrane was prehybridized at 42° C. in a 0.9M sodium chloride, 0.09M sodium citrate solution ("6× SSC"), 5× Denhardt's solution, 0.5% SDS (sodium dodecyl sulfate) and 100 $\mu$g/ml denatured carrier DNA. (See Manidatis et al.) Hybridizations were performed by the addition of oligodeoxyribonucleotide probes which had been radioactively labeled with gamma $^{32}$P-ATP using T4 polynucleotide kinase. After overnight hybridization, the filters were washed at room temperature for 15 min in 6× SSC, 0.5% SDS, and then at 56° C. for 30 min in 2× SSC, 05% SDS and subjected to autoradiography. One oligonucleotide probe (A) corresponded to nucleotides 127–151 of the FMR-I cDNA (5' CTGGGCCTCGAGCGCCCGCAGCCCA 3'); the other (B) was homologous to the CGG repeat region (5' [CGG]$_5$3') which corresponds to nucleotides 37–126.

EXAMPLE 1

DNA isolated from: (1) a normal individual (lanes 1); (2) a fragile X carrier male (lanes 2); (3) a male afflicted with the fragile X syndrome (lanes 3); and (4) a female fragile X carrier (lanes 4) were subjected to PCR in the presence of different proportions of 7-deaza-2'-dGTP to dGTP (100:0; 75:25; 50:50). The PCR products were analyzed by blot hybridization using a probe B (described above) complementary to the CGG repeat region of the FMR-1 locus. FIG. 1 shows the results of this analysis. Note that the high molecular weight bands were detected only in the presence of 100% 7-deaza-2'-dGTP, 0% dGTP. In other words, the fully mutated fragile X gene was only detected when the PCR reaction mixture was substantially free of dGTP.

EXAMPLE 2

Figure 2A:
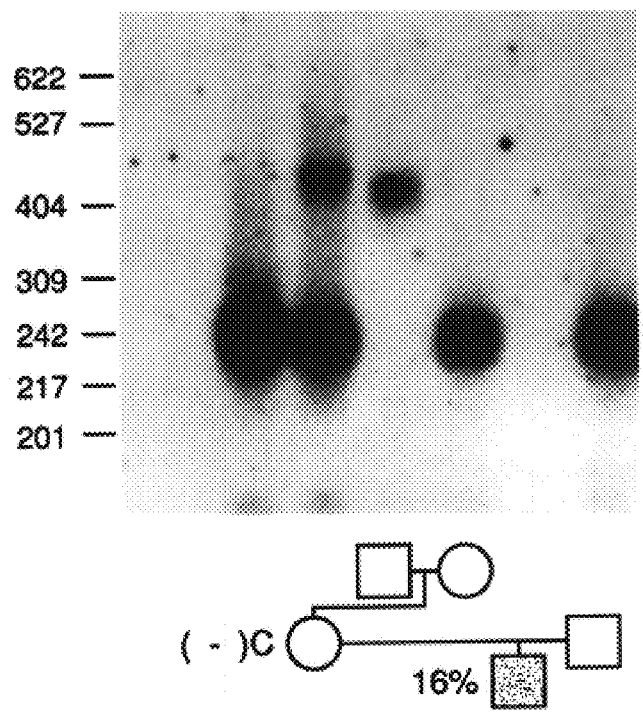
FIGS. 2A and B are photographs of two autoradiograms of PCR products from several members of a family including a fragile X positive grandson, as well as a chart showing the relationship among the several family members tested resolved by electrophoresis and Southern blot hybridization.
Figure 2B:
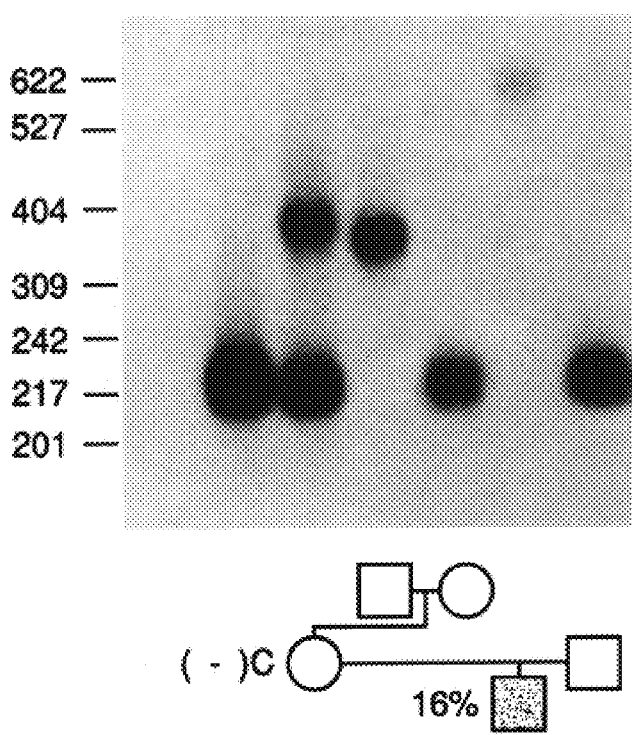

DNA samples were collected from fragile X family N43 and subjected to PCR, electrophoresis, and hybridization, as described above. The result of these analyses are illustrated in FIG. 2 (probe A results are on top and probe B on the bottom). Exposure times were 16 hours and 4 hours, respectively. Lane (−) is a no DNA control (primers only); lane (C) is a random control female DNA sample. DNA size markers, in bp, are indicated on the left. Only the 200 bp fragment was detected in DNAs from the non-carrier spouses: i.e., the afflicted individual's father and grandmother. A PCR product of approximately 400 bp was detected in the phenotypically normal carrier grandfather. The sequence was transmitted, with a small apparent increase in size, to his daughter. The fragile X positive grandson showed a PCR product of about 640 bp, indicating a significant increase in this region.

Sequential hybridization with probes A (FIG. 2A) and B (FIG. 2B) yielded similar patterns. However, the altered sequences were more readily detected with the B probe. This suggests that the alterations involve an amplification of the CGG sequence, thus increasing the amount of PCR product sequence which is homologous to the CGG probe (probe B).

EXAMPLE 3

Figure 3:
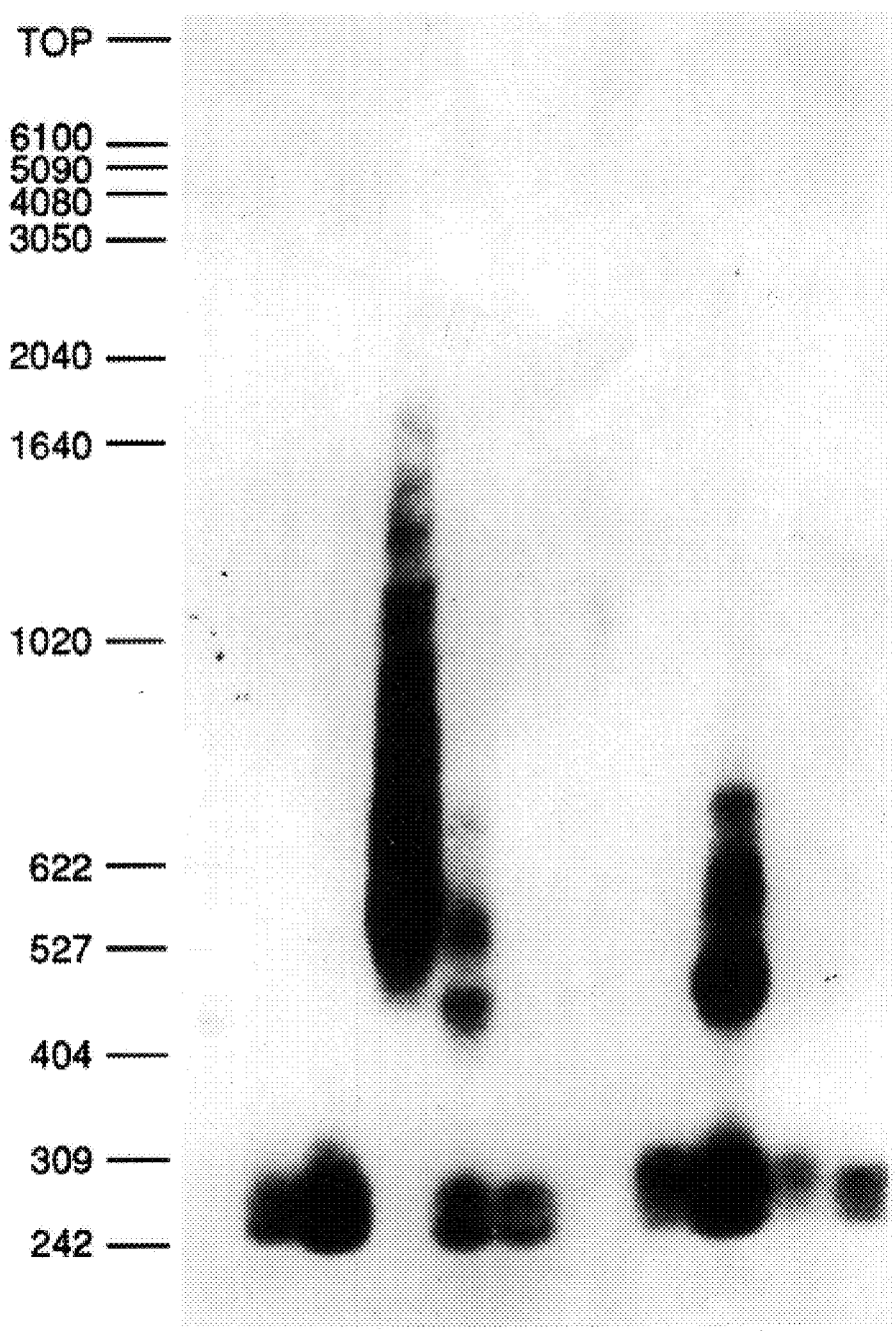
FIG. 3 is a photograph of an autoradiogram of PCR products from several members of another family including fragile X positive and negative grandchildren resolved by electrophoresis and Southern blot hybridization.
Figure 3:
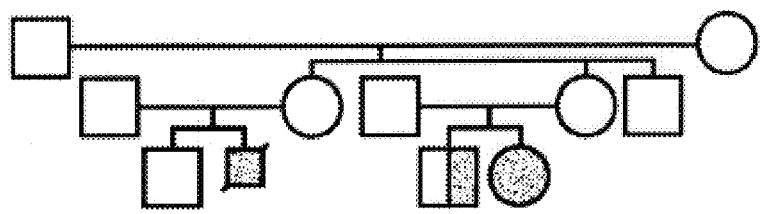

FIG. 3 illustrates the analysis of a second family (fragile X family N6) using the method of the present invention with only probe B. In this family, DNA markers had indicated that the grandfather was most likely a carrier and both of his daughters were known carriers. The analysis was performed as described in Example 2, except that only probe B was used. Exposure time was 3 hours. The carrier grandfather transmitted his amplified region, seen as a band of approximately 400 bp, to both of his carrier daughters. Both daughters show similar complex amplification patterns: in addition to the normal 200 bp band, both had bands of approximately 400, 530 and 650 bp.

One daughter had an unaffected son with a normal band of 200 bp. A second pregnancy resulted in a cytogenetically positive male fetus which was terminated. DNA from this prenatal specimen lacked a normal band, but instead contained a heterogeneous smear extending from 400 to approximately 5000 bp.

The other daughter had a cytogenetically positive, affected daughter with a 200 bp band and a faint band of approximately 400 bp. Her affected son showed an amplified band of approximately 1000 bp. This son, his sister and parents have been previously studied by genomic Southern blot analysis using probe Ox1.9, and by cytogenetics (family 5; figure Sd; Nakahori et al., Molecular Heterogeneity of the Fragile X Syndrome, Nucl. Acids Res. 19 4355–59, 1991). The affected son was of interest because he had been cytogenetically negative on several occasions. In the latter study, the carrier mother showed no abnormal DNA pattern, whereas our study clearly indicated the presence of an altered band. In our study the affected daughter also showed a pattern similar to the mother, although the altered allele was of lesser intensity.

We have consistently observed similar results in studies of 38 affected males, 12 carrier males and 60 affected and unaffected carrier females, selected from 34 fragile X families. All affected males showed large bands and/or smears with probe B of up to 6 Kb in length.

The results illustrate the potential for using our modified PCR to rapidly provide information about the presence and nature of the fragile X mutation. With this approach, it should be possible to quickly define alterations at the FMR-1 locus. Since all affected fragile X individuals appear to have a mother who is a carrier (Brown, 1990), it is now feasible to offer screening tests using a PCR-based method for detection of all carriers. The pregnancies of carriers can be monitored and the risk for the fragile X syndrome greatly reduced or eliminated.

EXAMPLE 4

A peripheral blood sample from an individual believed to have an Epstein-Barr virus infection is collected. Primers for the GC-rich terminal repeat region of the Epstein-Barr nucleic acid sequence are added along with other PCR reagents. The results are then compared to a standard to determine the clonality of infection in the individual who provided the sample.

In summary, the present invention improves and extends the applicability of the PCR assay to GC-rich nucleic acid sequences. It makes possible for the first time the detection by the PCR method of high molecular weight species of GC-rich sequences present in the fragile X syndrome. The process is especially useful in detecting nucleic acid sequences that are initially present in only very small amounts and in detecting nucleotide variations using sequence-specific oligonucleotides. Also, the amplification process herein can be used for molecular cloning and sequencing. The process herein results in increased yields of amplified product, greater specificity, and fewer steps necessary to carry out the amplification procedure, over what has been previously disclosed. An advantage of the method of the present invention over the prior art is the ability to perform analysis of patient samples without necessitating the time and expense of tissue culture.

Other modifications of the above-described embodiments of the invention that are obvious to those of skill in the area of molecular biology and related disciplines are intended to be within the scope of the following claims.

We claim:

1. A method for ascertaining whether an individual is a carrier for, or afflicted with Fragile X comprising:
   a) obtaining a nucleic acid sample from said individual; and
   b) amplifying a nucleic acid in said nucleic acid sample by performing a polymerase chain reaction on said sample in a reaction mixture that is substantially free of GTP and dGTP, said reaction mixture comprising:
      (1) at least one primer selected from the group consisting of oligonucleotides that are capable of specifically hybridizing within the FMR-1 fragile site, and oligonucleotides capable of specifically hybridizing sufficiently near the FMR-1 GC-rich fragile site to yield a PCR product; and
      (2) a nucleotide analogue selected from the group consisting of 7-deaza GTP, inosine, and 7-deaza inosine; and
   c) determining the size of said amplified nucleic acid wherein the size indicates the number of CGG repeats in said amplified nucleic acid d) correlating the size of the amplified nucleic acid and/or number of repeats to whether said individual is a carrier for or afflicted with Fragile X.

2. The method of claim 1 wherein said nucleic acid is selected from the group consisting of DNA and cDNA.

3. The method of claim 1 wherein said primer is present in a molar ratio of at least about 1000:1 primer:complementary strand.

4. The method of claim 1 wherein said analysis step further comprises hybridizing said amplified nucleic acid with a nucleic acid sequence comprising a plurality of CGG repeats.

5. The method of claim 1 which comprises at least five PCR cycles.

6. The method of claim 5 which comprises the use of 7-deaza-2'-GTP.

7. The method of claim 5 which further comprises dispersing said triphosphates and primer in a buffer comprising 50 mM KCl, 10 mM Tris-HCl, pH 8.3, 15 mM $MgCl_2$, 0.001% (w/v) gelatin, with the addition of 0.5-1 µg denatured genomic DNA, 50 pmoles of each oligonucleotide primer, 2.5 units of Taq polymerase, and 10% DMSO.

8. A method according to claim 1 which further comprises analyzing the products of said amplification to ascertain the number of base pairs therein.

9. A method according to claim 1 comprising a first and second primer, wherein the first primer is capable of binding to the first strand of a double stranded nucleic acid containing the FMR-1 gene and the second primer is capable of binding to the second nucleic acid strand of said double stranded nucleic acid, said primers binding to sites that straddle the GCC repeat region of said gene.

10. A kit for determining whether an individual is a carrier for or afflicted with Fragile X, comprising:

a) oligonucleotide primers capable of hybridizing to nucleic acid sequences selected from the group of sequences that consist of (I) sequences that are present within the FMR-1 fragile site, and (II) sequences that are sufficiently near the FMR-1 fragile site to provide an amplified product, wherein said oligonucleotide primers flank the FMR-1 fragile site;

b) a nucleotide analog selected from the group consisting of 7-deaza GTP, inosine, and 7-deaza-inosine; and c) a PCR reaction mixture which is substantially free of added GTP and dGTP.

11. The kit according to claims 10 wherein said analogue is 7-deaza-2'-GTP.

12. A kit according to claim 10 which further comprises a probe capable of hybridizing to FMR-1.

13. A kit according to claim 12 wherein said probe comprises a label.

14. A kit according to claim 11 which further comprises a probe consisting essentially of a plurality of 5' 3' repeat units.

15. A kit according to claim 14 wherein said probe comprises a label.

* * * * *